United States Patent
Schatz et al.

(10) Patent No.: US 6,398,551 B1
(45) Date of Patent: Jun. 4, 2002

(54) ANGLE PIECE FOR DENTAL OR SURGICAL USE

(75) Inventors: Norbert Schatz; Richard Kardeis, both of Bürmoos; Andreas Bachmaier, Oberndorf, all of (AT)

(73) Assignee: W & H Dentalwerk Bürmoos GmbH, Bürmoos (AT)

( * ) Notice: Subject to any disclaimer, the term of this patent is extended or adjusted under 35 U.S.C. 154(b) by 0 days.

(21) Appl. No.: 09/670,109

(22) Filed: Sep. 26, 2000

(30) Foreign Application Priority Data

Sep. 27, 1999 (AT) .............................................. 1656/99
Apr. 17, 2000 (AT) .............................................. 0676/00

(51) Int. Cl.⁷ ................................................ A61C 1/08
(52) U.S. Cl. ..................................................... 433/126
(58) Field of Search ................................ 433/126, 127, 433/128, 129, 133

(56) References Cited

U.S. PATENT DOCUMENTS

| | | | | |
|---|---|---|---|---|
| 2,370,632 A | * | 3/1945 | Blair | 433/126 |
| 3,909,946 A | * | 10/1975 | Watanabe | 433/126 |
| 4,403,956 A | * | 9/1983 | Nakanishi | 433/126 |
| 5,020,994 A | * | 6/1991 | Huang | 433/126 |
| 5,074,788 A | * | 12/1991 | Nakanishi | 433/129 |
| 6,206,694 B1 | * | 3/2001 | Swan | 433/129 |

* cited by examiner

Primary Examiner—Todd E. Manahan
(74) Attorney, Agent, or Firm—Friedrich Kueffner

(57) ABSTRACT

A collapsible angle piece for dental or surgical use has a head part, an elbow part detachably connected to the head part, and a handle detachably connected to the elbow part remote from the head part and having an actuating surface. The elbow part has a cage that is axially moveable between a locking position and a release position. At least one locking element is radially moveably supported in the cage, wherein the at least one locking element can be in a radially inner position or a radially outer position depending on whether the cage is in the locking position or in the release position. At least one elongate actuating member is arranged in the elbow part so as to be substantially axially moveable, wherein the at least one elongate actuating member has a first end cooperating with the cage and a second end cooperating with the actuating surface of the handle.

12 Claims, 4 Drawing Sheets

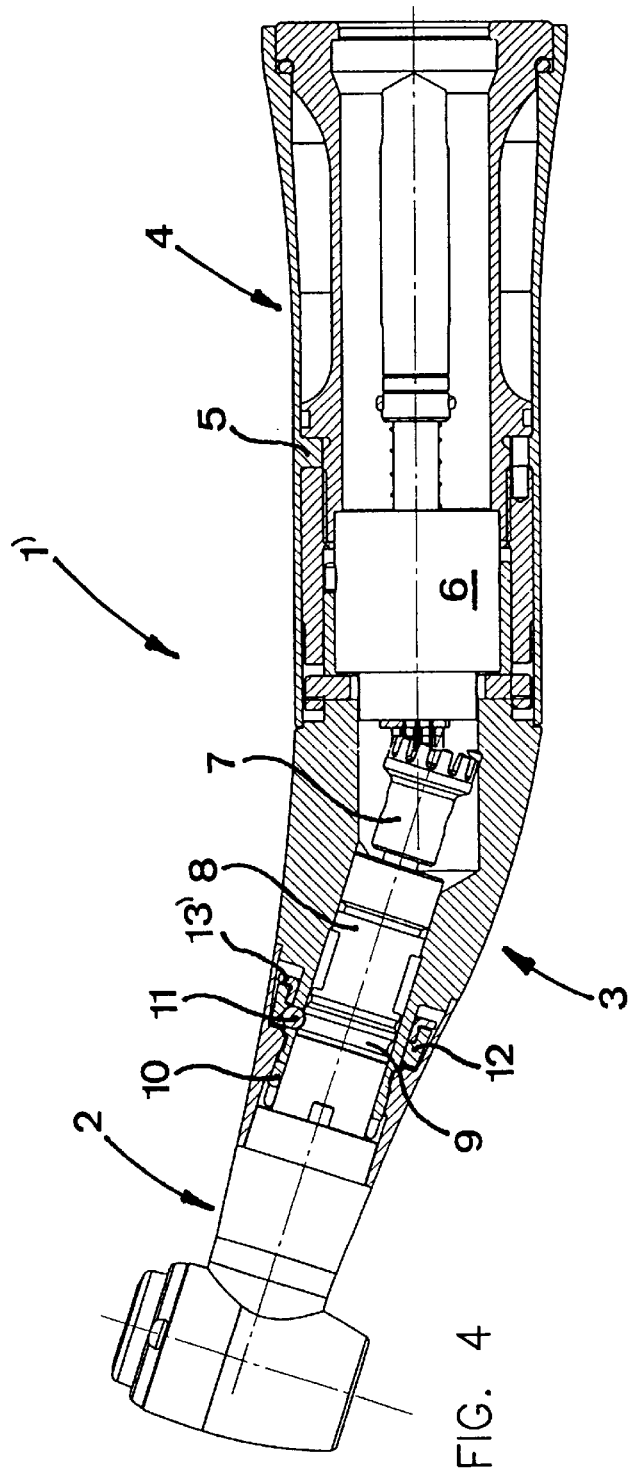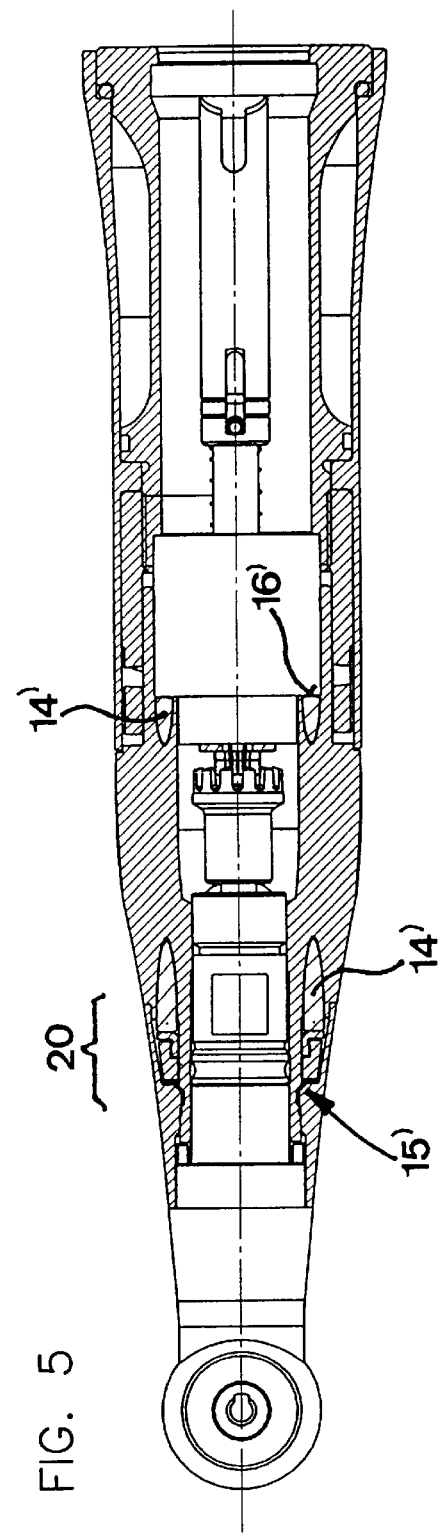
FIG. 4
FIG. 5

ANGLE PIECE FOR DENTAL OR SURGICAL USE

BACKGROUND OF THE INVENTION

1. Field of the Invention

The invention relates to an instrument in the form of an angle piece for dental or surgical use, comprising a head part, an elbow part, and a handle, and having improved collapsibility.

2. Description of the Related Art

An angle piece of this kind can be disassembled by loosening screws or the like, which method has been generally successfully used in the past.

However, in the course of more stringent hygiene regulations, and primarily in regard to angle pieces for surgical use which are employed in invasive surgery, it is now required to perform such a disassembly of an angle piece much more often than was conventionally done only a few years ago. This has the consequence that the disassembly process is considered to be cumbersome, and, therefore, there is a need for simplifying this process.

SUMMARY OF THE INVENTION

It is an object of the present invention to provide an angle piece of the aforementioned kind which fulfills these requirements.

In accordance with the present invention, this is achieved in that in the elbow part a cage is provided which can be axially moved between two positions, wherein one position is a locking position and the other is a release position, wherein at least one locking element is radially moveably supported in the cage which, as a function of the cage position, is in an inner or an outer position, and that in the elbow part at least one elongate actuating member is substantially axially slidably supported which with one end cooperates with the cage and with the other end with an actuating surface of the handle.

With the solution according to the invention, the angle piece can be disassembled in a simple manner into its three main components without requiring a tool or a complex procedure.

According to a first embodiment of the invention, the elongate actuation member is a pull rod and the actuation surface in the handle is a part of a rotatable catch element. The disassembly can be realized and the angle piece collapsed, for example, by rotating the handle relative to the elbow part.

According to a second embodiment of the invention the elongate actuating member is a push rod and the actuating surface of the handle is an end face of the handle. According to this embodiment, the handle can be designed especially compact and simple; the connection between the handle and the elbow part can be realized by means of any conventional connection known in the field of angle piece construction. The connection between the elbow part and handle can be realized by conventional snap-on technology, by means of a bayonet closure, by threadable coupling sleeves and the like.

BRIEF DESCRIPTION OF THE DRAWING

In the drawing:

FIG. 4 is a schematic illustration of another embodiment of the angle piece according to the invention, partly in a sectional view along the center plane; and FIG. 5 is a sectional view substantially perpendicular to the section of FIG. 4 and showing the respective axes of rotation of the drive connection, wherein the illustrated section plane and representation, especially in the area of the crown toothing, does not follow strictly the indicated section line.

DESCRIPTION OF THE PREFERRED EMBODIMENTS

Figure 1:
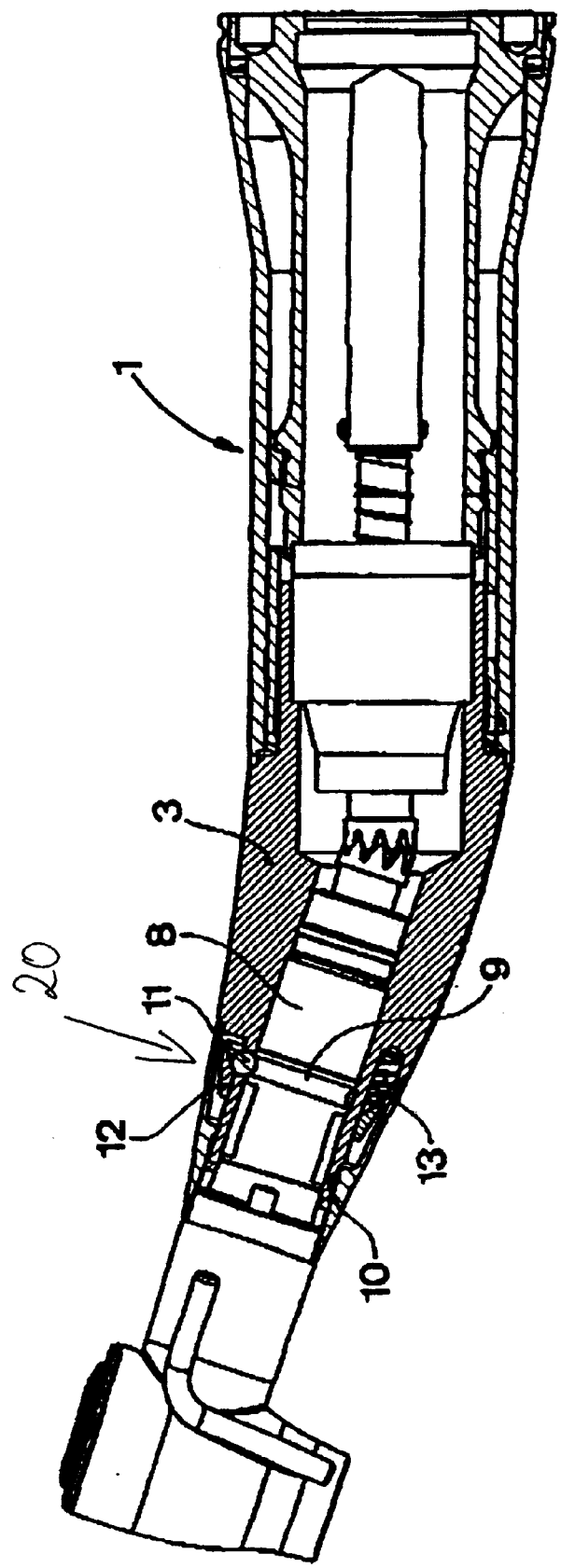
FIG. 1 is a section of a first variant of the angle piece according to the invention.
Figure 2:
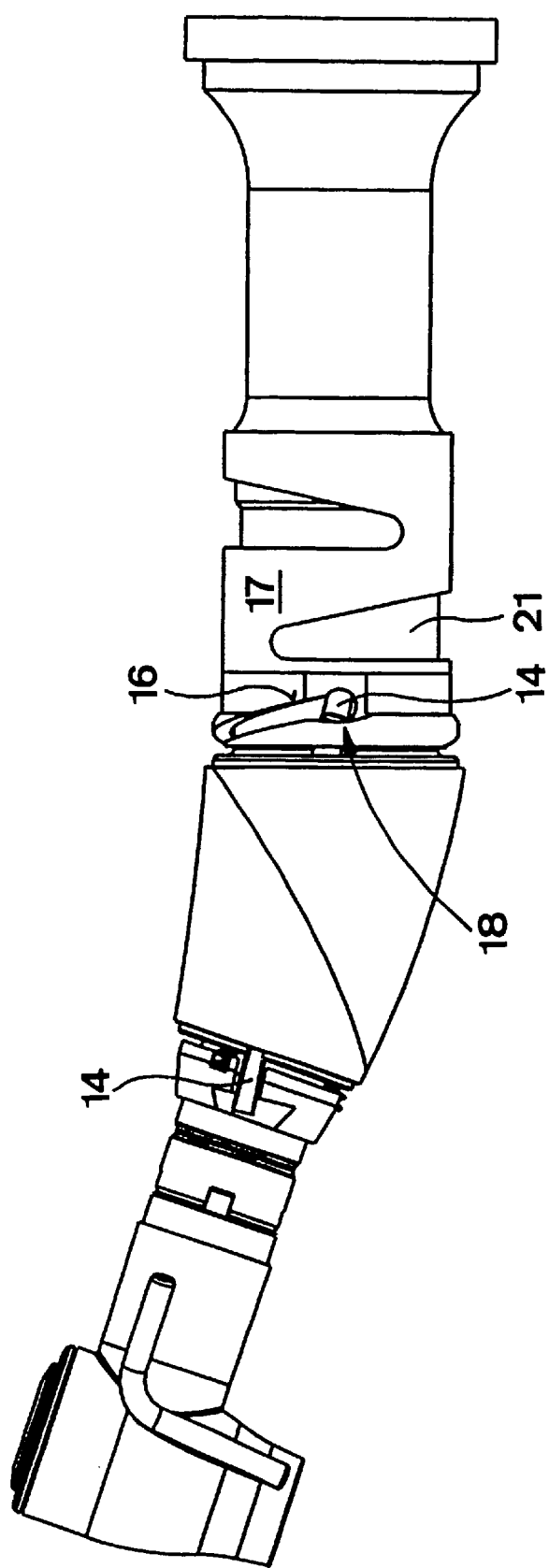
FIG. 2 is a side view of the angle piece according to FIG. 1 without sleeves in the area of the head part and the handle.
Figure 3:
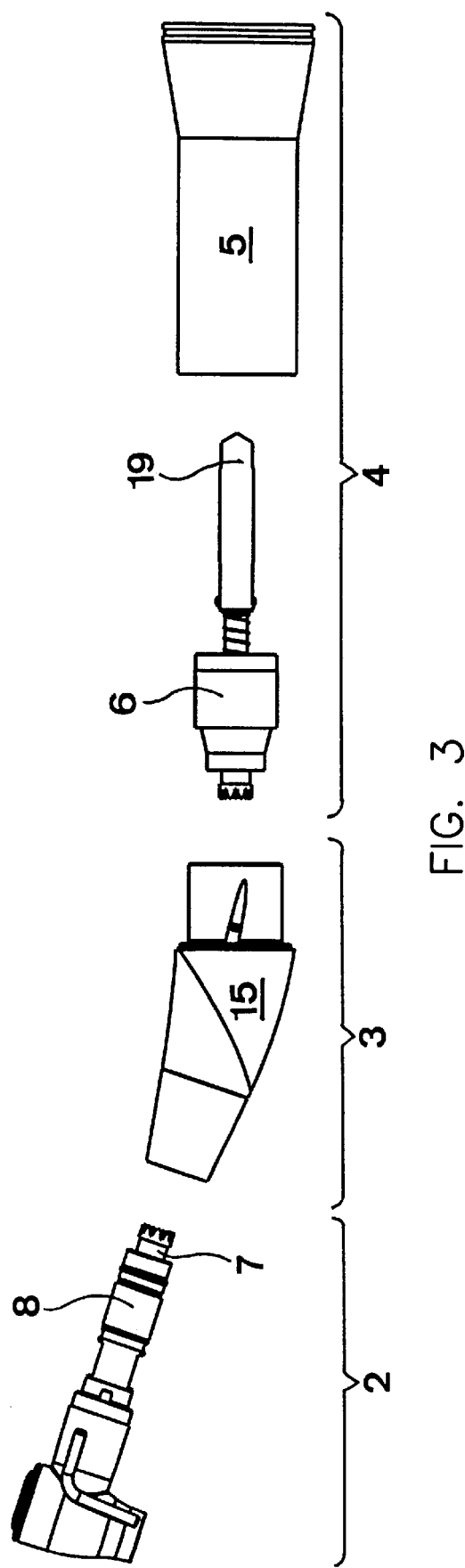
FIG. 3 is an exploded view of the disassembled angle piece of FIG. 1.

FIG. 1 shows in section an angle piece 1 according to the invention in the assembled state, FIG. 2 shows a plan view in analogy to FIG. 1 but partially without outer covering (sleeves). As can be seen in particular in FIG. 3, the angle piece 1 can be disassembled into three parts or components according to the invention as follows:

A head part 2, an elbow part 3, and a handle 4. In the illustrated embodiment the disassembly process according to the invention entails separating the handle 4 also into two parts, a sleeve part 5 and a drive part 6. The corresponding driven shaft 7 remains at the head part 2 and its end portion provided with the crown toothing cooperates in the assembled state with a correspondingly shaped end portion of the drive part 6.

The device according to the invention which ensures the connection of the parts can be seen best with the aid of FIGS. 1 and 2.

The head part 2 has a substantially cylindrical tubular part 8 surrounding the shaft 7 and is provided with a circumferential groove 9. The elbow part 3 projects with a cylindrical extension 10 so as to surround the tubular part 8. The cylindrical extension 10 has openings in an area, which in the assembled state of the angle piece 1 is positioned opposite to the circumferential groove 9. Locking elements, in the shown embodiment, locking balls 11, are supported in the openings. These openings and thus the locking balls 11 have correlated therewith a conical ring 12 which is acted upon by at least one spring 13. The at least one spring 13 forces the conical ring 12 in a direction in which the cone shape of the conical ring 12 permits a radially outwardly oriented movement of the locking balls 11 out of the area of the circumferential groove 9. All of these components form thus an actuatable cage 20 for the locking balls 11 at the elbow part side.

Two elongate actuating members are connected to the conical ring 12, preferably articulated on the conical ring 12, and in the shown embodiment are formed as pull rods 14 (FIG. 2). These pull rods project at the end of the elbow part 3 facing the handle 4 to such an extent from the sleeve 15 of the elbow part 3 that their ends (in the assembled state of the angle piece 1) are positioned in the area of the ramp 16 of a catch element 17 in the interior of the sleeve part 5.

The ramp 16, as is illustrated in particular in FIG. 2, is designed such that, upon rotation of the catch element 17 about approximately 90° with respect to the represented position, the end of the ramp 16 reaches the area of the pull rod 14 so that a notch or a bent portion of the pull rod, upon placement and rotation of the catch element 17, reaches the area of the ramp and cooperates with it such that the pull rod 14 is pulled toward the handle 4. As a result of this movement, the conical ring 12 is pulled counter to the force of the spring(s) 13 also in the direction toward the handle 4 and the locking balls 11 are forced through the correlated openings into the area of the circumferential groove 9. By this measure, the head part 2 is combined with the handle 4 with interposition of the elbow part 3 and the three parts are fixedly connected to one another by the pulling action of the pull rod(s) 14. In this connection, it should be noted that the catch element 17 is fixedly connected, or at least connected for common rotation, with the handle 4, especially with its sleeve part 5.

With the disclosed device according to the invention, an angle piece is now provided which is collapsible and does not require a tool for mounting and demounting.

With the formation of the ramp, as shown in FIG. 2, which in the area of the locking position has a depression 18, disassembly can take place only when the pull rod 14 reaches past the edge of this depression 18 into the actual ramp area. This requires a considerable moment so that an erroneous or accidental unlocking, caused by vibration, impact and the like, and thus demounting are not possible.

In the illustrated embodiment, two pull rods 14, three locking balls 11, and three springs 13 are provided; however, a person skilled in the art can easily envision and realize other embodiments. For example, it is especially possible to employ plate springs or a plate spring package instead of the coil spring(s) 9 so that mounting is facilitated in the case of total disassembly or for manufacture of the instrument.

In the illustrated embodiment, the end of the pull rods 14 facing the head part 2 is supported in a larger recess of the conical ring in order not to impair the movements of the conical ring and in order to be able to work with greater tolerances. The pull rods 14 may have their actual support in the interior of the elbow part 3; for their proper function it is only important that they are secured against rotation about the handle axis in the area of the end facing the handle in order to be able to reliably reach the ramp 16, and not to turn in a position in front of this ramp, when the catch element 17 is rotated.

The catch element 17 in the illustrated embodiment has at least one thread-shaped cutout 21 by means of which it can be spring-elastic in the axial direction so that, on the one hand, it can compensate tolerances and, on the other hand, the application of a pretension onto the pulling rods 14 is made possible.

With the configuration of the angle pieces 1 according to the invention it is advantageous, and in most cases necessary, to design the engagement part 19 of the drive part 6 so as to be movable in the axial direction in order to compensate axial tolerances of the individual components. In the illustrated embodiment this is realized by means of a pressure spring which is arranged between the bearing part of the drive part 6 and the engagement part 19. This spring arrangement, of course, may not compromise the rotational securing of the connection of the two parts of the shaft.

It is not necessary to carry out the axial compensation of the tolerances in the way illustrated and disclosed; a person skilled in the art of medical angle pieces, with knowledge of the invention, has several measures at his disposal in order to achieve this. Also, the at least one spring 13 must not be provided or must not be arranged as illustrated; instead, a plate spring or spring washer can be provided. The same holds true for the thread-shaped cutouts 21 by which the catch element 17 obtains its spring action.

In FIGS. 4 and 5 a variant according to the invention is illustrated in which two elongate actuating members are provided which are formed as push rods. Same parts are identified with the same reference numerals as in FIGS. 1 through 3.

The angle piece 1' according to the invention is comprised substantially of a head part 2, an elbow part 3, and a handle 4. In the illustrated embodiment the handle 4 is comprised of a sleeve part 5 and a drive part 6 which is arranged in the interior of the sleeve part 5. A shaft 7 extends in the elbow part 3 and in the head part 2 and is provided at the end remote from the head part 2 with a crown toothing for cooperation with the end of the drive part 6 facing the head part; in this way, the drive action of the tool (not illustrated) is realized.

In the head part 2 there is a substantially cylindrical tubular part 8 surrounding the shaft 7 which is provided with a circumferential groove 9. It is possible to use recesses instead of the circumferential groove, for example, cup-shaped milled portions, at appropriate locations. The elbow part 3 projects with its cylindrical extension 10 across the tubular part 8 and surrounds it. The cylindrical extension 10 comprises openings in an area which, in the assembled state of the angle piece 1', is positioned opposite the circumferential groove 9, and the locking elements, in the illustrated embodiment locking balls 11, are supported in these openings. Correlated with these openings, and thus also with the locking balls 11, is a ring 12, which is conical at least in the area of the locking balls 11. The conical ring 12 forces the locking balls 11 radially inwardly into the area of the circumferential groove 9 (or of the single recesses).

In addition, at least one spring with minimal force can be provided; in the illustrated embodiment this is a spring washer (hardly visible in the drawing) between the conical ring 12 and the ring collar 13' with L-shaped cross-section. It forces the conical ring 12 in a direction in which its cone shape forces the locking balls 11 radially slightly inwardly and, together with the annular groove, provides for an easy snap connection. This means that the head part 2 and the elbow part 3 are fixated in their position relative to one another and an accidental detachment is prevented; however, the two parts can be separated from one another by applying a light axial pulling action. All of these components thus form a cage 20 for the locking balls 11 which cage is located on the elbow part 3 of the angle piece 1' according to the invention.

This cage 20 of the elbow part 3 can be actuated by means of at least one push rod 14', in the illustrated embodiment two push rods, which bring the conical ring 12 via the annular collar 13' and the spring into a position in which the locking balls 11 are forced radially inwardly into the circumferential groove 9 so that they ensure a safe and position-exact locking between the head part 2 and the elbow part 3. The movement of the push rods 14 is realized again by the assembly of the handle 4 with the elbow part 3, wherein the end faces 16' move the rearward ends of the push rods 14 against the head counter to the force of the spring. The end faces 16' must not be provided discretely and particularly on the drive part 6 or the sleeve part 5 but can be simply formed thereat by means of shoulders, a projection or the like.

The connection between handle 4 and elbow part 3 can be realized in a conventional way, for example, by a clip connection which, by means of elastic deformation, allows a sleeve to be slipped on, wherein the detachment is realized either by a rotary movement, by actuation of a release mechanism or by applying stronger pulling forces. However, the connection can also be realized by a type of coupling sleeve with a screw connection or by another connection type known from the prior art.

In order to facilitate assembly, a clip or bayonet connection, as indicated by the reference numeral 15', can be provided for connecting the head part 2 and the elbow part 3, wherein this clip or bayonet closure secures the two parts in their correct position to one another until the locking balls 11 take over this function with sufficient force and precision.

As long as the push rods 14' are not forced by the connection of the handle 4 to the elbow part 3 in a direction toward the head part 2, the annular collar 13' is relatively freely movable and the spring whose spring travel is small releases the conical ring 12 to such an extent that the locking balls 11 can radially exit from the circumferential groove 9 so that they make a separation of the elbow part 3 from the head part 2 possible.

The spring itself contributes to easier mounting, but is provided essentially for compensating possible tolerances in the longitudinal direction of the assembled angle piece 1.

The invention is not limited to the illustrated embodiment but can also be configured differently. For example, as already mentioned above, it is possible to eliminate the spring between the annular collar 13' and the conical ring 12 when the tolerances are respectively tight. In this case, the ring collar can be eliminated also, respectively, it can be combined with the conical ring to a single component. If a compensation of tolerances is still desired in this case, a compensation spring can be provided between the elbow part 3 and the handle 4.

When using the illustrated configuration, it is beneficial to select the axial movability of the annular collar 13' distinctly greater than the spring travel of the spring in order to be able to move the conical ring, when the push rods 14 are not in contact at the end face 16, such that it provides the locking balls 11 with a sufficiently great radial movability in order to be able to separate the head part 2 easily from the elbow part 3.

The dimensions and support of the locking elements must not be realized as illustrated, but can instead be designed differently, especially when the locking elements used are not ball-shaped.

As a material for the cage, the balls, and the actuating elements all materials employed in similar situations and known to a person skilled in the art of medical instruments can be used, so that a person skilled in the art can easily make an appropriate selection in view of the knowledge of the invention.

While specific embodiments of the invention have been shown and described in detail to illustrate the inventive principles, it will be understood that the invention may be embodied otherwise without departing from such principles.

What is claimed is:

1. A collapsible angle piece for dental or surgical use, the angle piece comprising:

a head part;

an elbow part detachably connected to the head part;

a handle detachably connected to the elbow part remote from the head part and having an actuating surface;

wherein the elbow part comprises a cage configured to be axially moveable between a locking position and a release position;

at least one locking element radially moveably supported in the cage, wherein the at least one locking element is configured to be in a radially inner position or a radially outer position depending on whether the cage is in the locking position or in the release position;

at least one elongate actuating member arranged in the elbow part so as to be substantially axially moveable, wherein the at least one elongate actuating member has a first end configured to cooperate with the cage and a second end configured to cooperate with the actuating surface of the handle.

2. The angle piece according to claim 1, wherein the at least one actuating member is a pull rod and wherein the handle has a rotatable catch element with a ramp forming the actuating surface of the handle cooperating with the second end of the pull rod.

3. The angle piece according to claim 2, wherein the catch element has at least one thread-shaped cutout.

4. The angle piece according to claim 2, wherein the ramp has a depression and wherein the second end of the pull rod rests in the depression in the assembled state of the angle piece.

5. The angle piece according to claim 2, wherein two of the pull rods are provided and are positioned substantially diametrically opposite one another relative to an axis of the angle piece in the area of the cage.

6. The angle piece according to claim 1, wherein the at least one actuating member is a push rod and wherein the actuating surface of the handle is the end face of the handle.

7. The angle piece according to claim 6, wherein the elbow part has an annular collar and a spring arranged between the annular collar and the cage, wherein the push rod acts on the annular collar and wherein the annular collar is configured to transmit a pressure force exerted by the push rod onto the cage via the spring.

8. The angle piece according to claim 7, wherein several of the push rods act on the annular collar.

9. The angle piece according to claim 1, wherein the at least one locking element is a ball.

10. The angle piece according to claim 1, wherein the head part has a recess and wherein the at least one locking element is configured to engage the recess in the radially inner position.

11. The angle piece according to claim 10, wherein the recess is a circumferential groove.

12. The angle piece according to claim 10, wherein the cage is a conical ring and wherein the elbow part has a spring acting on the conical ring so as to force the conical ring in a direction in which a cone shape of the conical ring allows a radially outwardly directed movement of the at least one locking element out of the recess.

* * * * *